(12) United States Patent
Drovetskaya et al.

(10) Patent No.: US 10,507,176 B2
(45) Date of Patent: *Dec. 17, 2019

(54) HAIR CARE COMPOSITIONS CONTAINING CATIONIC POLYMERS

(71) Applicant: Dow Global Technologies LLC, Midland, MI (US)

(72) Inventors: Tatiana V. Drovetskaya, Martinsville, NJ (US); Susan L. Jordan, Collegeville, PA (US); Thomas H. Kalantar, Midland, MI (US); Mladen Ladika, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/527,427

(22) PCT Filed: Nov. 17, 2015

(86) PCT No.: PCT/US2015/061054
§ 371 (c)(1),
(2) Date: May 17, 2017

(87) PCT Pub. No.: WO2016/085706
PCT Pub. Date: Jun. 2, 2016

(65) Prior Publication Data
US 2017/0354586 A1    Dec. 14, 2017

Related U.S. Application Data

(60) Provisional application No. 62/084,134, filed on Nov. 25, 2014.

(51) Int. Cl.
*A61K 9/70* (2006.01)
*A61K 8/81* (2006.01)
(Continued)

(52) U.S. Cl.
CPC .......... *A61K 8/8158* (2013.01); *A61K 8/817* (2013.01); *A61Q 5/02* (2013.01); *A61Q 5/12* (2013.01)

(58) Field of Classification Search
CPC .... A61K 8/8158; A61K 8/817; A61K 8/8188; A61K 8/8182; A61Q 5/02; A61Q 5/12; A61Q 5/06; A61Q 5/004; C08F 222/38
See application file for complete search history.

(56) References Cited

U.S. PATENT DOCUMENTS 5,338,541 A    8/1994  Matz et al.
5,609,862 A *  3/1997  Chen ................... A61K 8/8158
                                              132/203

(Continued)

FOREIGN PATENT DOCUMENTS

CA         2517317 A1    2/2006
JP       2012020968 A    2/2012
(Continued)

*Primary Examiner* — Lakshmi S Channavajjala

(57) ABSTRACT

Provided are compositions and methods that are useful for personal care compositions. The compositions comprise (a) a cationic polymer comprising polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) at least one cosmetically acceptable surfactant, rheology modifier, or cosmetic active. Also provided are methods of treating hair with such compositions.

6 Claims, 1 Drawing Sheet

(51) Int. Cl.
*A61Q 5/02* (2006.01)
*A61Q 5/12* (2006.01)

(56) References Cited

U.S. PATENT DOCUMENTS

| | | |
|---|---|---|
| 5,637,306 A | 6/1997 | Cauwet et al. |
| 6,849,584 B2 | 2/2005 | Geary et al. |
| 7,015,279 B2 | 3/2006 | Braun et al. |
| 7,405,188 B2 | 7/2008 | Chen |
| 9,499,648 B2 * | 11/2016 | Blondel .................. C08F 36/20 |
| 2003/0059382 A1 * | 3/2003 | Brandt .................. A61K 8/8158 424/59 |
| 2005/0100523 A1 | 5/2005 | Maubru et al. |
| 2006/0024338 A1 | 2/2006 | Hegedus et al. |
| 2017/0354586 A1 | 12/2017 | Drovetskaya et al. |

FOREIGN PATENT DOCUMENTS

| | | |
|---|---|---|
| WO | 200037041 A1 | 6/2000 |
| WO | 2002083085 A1 | 10/2002 |
| WO | 2004069979 A2 | 8/2004 |
| WO | 2005002532 A2 | 1/2005 |
| WO | 2006058755 A1 | 6/2006 |
| WO | 2006081496 A2 | 8/2006 |
| WO | 2007098888 A1 | 9/2007 |
| WO | 2007128639 A2 | 11/2007 |
| WO | 2009024936 A2 | 2/2009 |
| WO | WO2014118465 A1 * | 8/2014 |

* cited by examiner

HAIR CARE COMPOSITIONS CONTAINING CATIONIC POLYMERS

FIELD OF THE INVENTION

This invention relates generally to cationic polymers and their use in hair care compositions. The cationic polymers contain as polymerized units cationic monomers, (meth) acrylamide monomers, and polar non-ionic derivatives of acrylic monomers.

BACKGROUND

Conditioning of hair is one of the most desired attributes in a personal care composition, particularly conditioners. Unless a conditioning agent is utilized, hair is often difficult to manage during and after shampooing. From an end-user perspective, consumers associate good aesthetics, such as pleasant tactile feel and a pleasing visual appearance, with performance and value. For conditioning compositions, it is also desirable that such compositions provide smoothness, while leaving the hair with a light and natural feel.

To this end, combinations of silicones and cationic polymers have been utilized. For example, PCT International Publication No. WO 2000/37041 discloses keratin conditioning formulations containing a water soluble, organic, ampholytic polymer and a water soluble, organic, cationic polymer. The prior art falls short, however, of delivering optimal conditioning properties while maintaining hair in a clean, non-greasy appearance after shampoo application.

Consequently, there is a continuing need to develop new cost-effective high performance conditioning agents that provide pleasant tactile feel and pleasing visual appearance, while also providing for increased manageability when applied to hair.

STATEMENT OF INVENTION

One aspect of the invention provides a hair care composition comprising (a) a cationic polymer comprising polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) at least one cosmetically acceptable surfactant, rheology modifier, or cosmetic active. In certain embodiments, the hair care composition comprises the polar non-ionic derivatives of acrylic monomers in an amount of from 2 to 30 weight %. In certain embodiments, the personal care composition is a leave-on conditioner, a hair treatment formulation, a combing cream, or a shampoo.

In another aspect, the invention provides a method for treating hair comprising contacting hair with a hair care composition comprising (a) a cationic polymer comprising polymerized units derived from (i) 30 to 80 weight % of cationic monomers, (ii) 10 to 65 weight % of (meth) acrylamide monomers, and (iii) 0 to 30 weight % of polar non-ionic derivatives of acrylic monomers, and (b) at least one cosmetically acceptable surfactant, rheology modifier, or cosmetic active. In certain embodiments, the personal care composition comprises the polar non-ionic derivatives of acrylic monomers in an amount of from 2 to 30 weight %. In certain embodiments, the hair care composition is a leave-on conditioner, a hair treatment formulation, or a combing cream.

DETAILED DESCRIPTION

Figure 1:
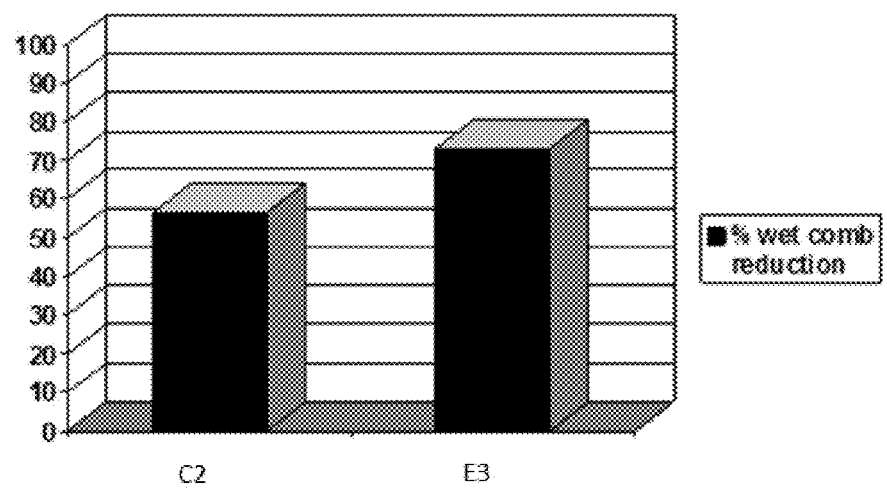
FIG. 1 show the objective wet combing performance of hair care formulations containing inventive and comparative conditioning agents in the absence of silicone.

The inventors have now surprisingly found that hair care compositions containing cationic polymers containing, as polymerized units, a cationic monomer, an acrylamide monomer, and a polar non-ionic derivative of an acrylic monomer, provide a pleasant tactile feel and a pleasing visual appearance, while also providing for increased manageability when applied to hair. Accordingly, in certain preferred embodiments the present invention provides in one aspect personal care compositions including cationic polymers containing polymerized units derived from (a) cationic polymers containing polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) at least one cosmetically acceptable surfactant, rheology modifier, or cosmetic active.

In the present invention, "hair care" is intended to refer to hair care compositions including, for example, shampoos, rinse-off conditioners, leave-on conditioners, styling gels, hairsprays, mousses, pomades, hair treatment formulations, and combing creams. Preferably, the hair care compositions are cosmetically acceptable. As used herein, "cosmetically acceptable" refers to ingredients typically used in personal care compositions, and is intended to underscore that materials that are toxic when present in the amounts typically found in hair care compositions are not contemplated as part of the present invention. The hair care compositions of the invention may be manufactured by processes well known in the art, for example, by means of conventional mixing, dissolving, granulating, emulsifying, encapsulating, entrapping, or lyophilizing processes.

As used herein, the term "polymer" refers to a polymeric compound prepared by polymerizing monomers, whether of the same or a different type. The generic term "polymer" includes the terms "homopolymer," "copolymer," and "terpolymer." As used herein, the term "polymerized units derived from" refers to polymer molecules that are synthesized according to polymerization techniques wherein a product polymer contains "polymerized units derived from" the constituent monomers which are the starting materials for the polymerization reactions.

The inventive compositions include cationic polymers that contain polymerized units derived from cationic monomers. Cationic monomers are compounds that form polymerized units in which at least one cation is covalently attached to the polymer. The anion or anions corresponding to the covalently-attached cation or cations may be in solution, in a complex with the cation, located elsewhere on the polymer, or a combination thereof. The anion corresponding to the cation of a suitable cationic monomer may be any type of anion. Some suitable anions are, for example, halides (including, for example, chloride, bromide, or iodide), hydroxide, phosphate, sulfate, hydrogen sulfate, ethyl sulfate, methyl sulfate, formate, acetate, or any mixture thereof.

In certain embodiments, the cationic monomers useful in the present invention contain a cation that is permanently in cationic form, such as, for example, a quaternary ammonium salt. Quaternary ammonium salt compounds that are suitable as cationic monomers include, for example, (meth)acrylamidealkyltrialkylammonium and [(meth)acryloyloxy]alkyltrialkylammonium quaternary compounds, and diallyldialkylammonium quaternary compounds, and mixtures thereof.

(Meth)acrylamido alkyl trialkyl ammonium and (meth) acryloyloxy alkyl trialkyl ammonium quaternary compounds have the general structure:

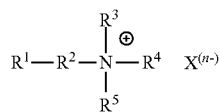

where $R^1$ is a (meth)acrylamido group, which has the general structure:

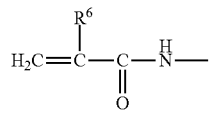

or a (meth)acryloyloxy group, which has the general structure:

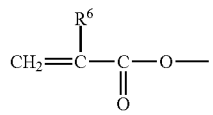

where $R^6$ is either hydrogen or a methyl group; $R^2$ is a bivalent alkyl group; each of $R^3$, $R^4$, and $R^5$ is, independently, a methyl ethyl, or butyl group; and $X^{(n-)}$ is an anion wherein n is 1, 2, or 3, for example any of the anions discussed herein above as suitable anions corresponding to cations of suitable cationic monomers. In certain embodiments, $R^6$ is hydrogen. In certain embodiments, $R^2$ is $-CH_2-CH_2-CH_2-$. Independently, in some embodiments, one, two, or all three of $R^3$, $R^4$, and $R^5$ are methyl groups. Independently, in some embodiments, $X^{(n-)}$ is a chloride ion.

Diallyldialkylammonium quaternary compounds have the general structure:

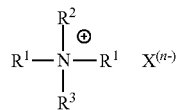

where each $R^1$ is an allyl group; each of $R^2$ and $R^3$ is, independently, an alkyl group with 1 to 3 carbon atoms; and $X^{(n-)}$ is an anion wherein n is 1, 2, or 3, for example any of the anions discussed herein above as suitable anions corresponding to cations of suitable cationic monomers. In some embodiments, each of $R^8$ and $R^9$ is a methyl group. Independently, in some embodiments, $X^{(n-)}$ is a chloride ion. In certain embodiments, the diallyldialkylammonium quaternary monomer forms a polymerized unit that is a 5-membered ring.

In certain preferred embodiments, the cationic monomer comprises at least one of diallyldimethylammonium chloride (DADMAC), [2-(acryloyloxy)ethyl]trimethylammonium chloride (AETAC), [2-(methacryloyloxy)ethyl]trimethylammonium chloride (QMA-Cl), (3-acrylamidopropyl)trimethylammonium chloride (APTAC), and (3-methacrylamidopropyl)trimethylammonium chloride (MAPTAC). In certain embodiments, the inventive cationic polymers comprise polymerized units derived from cationic monomers present in an amount of at least 30 weight %, preferably at least 35 weight %, more preferably at least 40 weight %, and even more preferably at least 45 weight %, by weight of the polymer. In certain embodiments, the inventive cationic polymers comprise the cationic monomers in an amount of no more than 80 weight %, preferably no more than 75 weight %, more preferably no more than 70 weight %, and even more preferably no more than 65 weight %, by weight of the polymer.

The inventive cationic polymers comprise polymerized units of (meth)acrylamide monomers and their derivatives. (Meth)acrylamide compounds have the general structure:

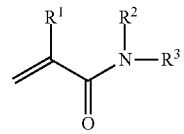

where $R^1$ is hydrogen or a methyl group; and each of $R^2$ and $R^3$ are, independently, hydrogen or a linear, branched or cyclic alkyl or aryl group having from 1 to 18 carbon atoms. In certain embodiments, the inventive cationic polymers comprise polymerized units of (meth)acrylamide monomers present in an amount of at least 10 weight %, preferably at least 15 weight %, more preferably at least 20 weight %, and even more preferably at least 25 weight %, by weight of the polymer. In certain embodiments, the inventive cationic polymers comprise the (meth)acrylamide monomers in an amount of no more than 65 weight %, preferably no more than 62.5 weight %, more preferably no more than 60 weight %, and even more preferably no more than 55 weight %, by weight of the polymer.

The inventive cationic polymers optionally comprise polymerized units of polar non-ionic derivatives of acrylic monomers. Suitable acrylic monomers include, for example, (meth)acrylic acids and their $C_1$-$C_{22}$ alkyl or hydroxyalkyl esters, including monomers of structure $H_2C=C(R)CO_2(CH_2CH_2O)_n(CH(R')CH_2O)_mR''$, crotonic acid, itaconic acid, fumaric acid, maleic acid, maleic anhydride, (meth)acrylamides, (meth)acrylonitrile, and alkyl or hydroxyalkyl esters of crotonic acid, itaconic acid, fumaric acid or maleic acid. In certain embodiments, the acrylic monomer comprises an aminoalkyl ester of (meth)acrylic acid, which has the general structure:

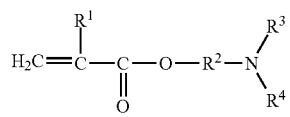

where $R^1$ is hydrogen or a methyl group; $R^2$ is a bivalent alkyl group; and each of $R^3$ and $R^4$ is, independently, a hydrogen, a methyl group, or an ethyl group. In certain embodiments, $R^1$ is a methyl group. In certain embodiments, $R^2$ is either $-CH_2-CH_2-$ or $-CH_2-CH_2-CH_2-$. In certain embodiments, $R^3$ and $R^4$ are both methyl groups.

Suitable monomers that are aminoalkyl esters of (meth) acrylic acid include, for example, 2-(dimethylamino)ethyl acrylate (DMAEA), 2-(dimethylamino)ethyl methacrylate (DMAEMA), and 3-dimethylaminopropyl acrylate (DMAPA). In certain embodiments, the inventive cationic polymers comprise polymerized units of polar non-ionic derivatives of acrylic monomers in an amount of at least 2 weight %, preferably at least 5 weight %, more preferably at least 7.5 weight %, and even more preferably at least 10 weight %, by weight of the polymer. In certain embodiments, the inventive cationic polymers comprise polymerized units of polar non-ionic derivatives of acrylic monomers in an amount of no more than 30 weight %, preferably no more than 27.5 weight %, more preferably no more than 25 weight %, and even more preferably no more than 20 weight %, by weight of the polymer.

In certain embodiments, the cationic polymer optionally further comprises polymerized units of non-polar $C_1$-$C_{22}$ alkyl (meth)acrylate monomers. Suitable non-polar monomers include, for example, methyl (meth)acrylate, butyl (meth)acrylate, 2-ethylhexyl (meth)acrylate, dodecyl (meth) acrylate, and stearyl (meth)acrylate). In certain embodiments, the inventive cationic polymers comprise polymerized units of non-polar monomers in an amount of at least 0.05 weight %, preferably at least 0.1 weight %, more preferably at least 0.5 weight %, and even more preferably at least 1.0 weight %, by weight of the polymer. In certain embodiments, the inventive cationic polymers comprise polymerized units of non-polar monomers in an amount of no more than 10 weight %, preferably no more than 8.75 weight %, more preferably no more than 7.5 weight %, and even more preferably no more than 5.0 weight %, by weight of the polymer.

Polymer molecular weights can be measured by standard methods such as, for example, size exclusion chromatography or intrinsic viscosity. In certain embodiments, the cationic polymer of the present invention has a weight average molecular weight ($M_w$) of 2,000,000 or less, preferably 1,500,000 or less, more preferably 1,250,000 or less, and even more preferably 1,000,000 or less. In certain embodiments, the cationic polymer has a $M_w$ of 50,000 or more, preferably 100,000 or more, preferably 150,000 or more, and even more preferably 250,000 or more.

The cationic polymer of the present invention may be made by any polymerization method, including, for example, solution polymerization, bulk polymerization, heterogeneous phase polymerization (including, for example, emulsion polymerization, suspension polymerization, dispersion polymerization, and inverse-emulsion polymerization), and combinations thereof. Independently, the ampholytic polymer of the present invention may be made with any type of polymerization reaction, including, for example, free radical polymerization. When solution polymerization is used, the solvent may be an aqueous solvent (i.e., the solvent is 75% or more water, by weight, based on the weight of the solvent) or an organic solvent (i.e., a solvent that is not aqueous). In certain embodiments, at least one ampholytic polymer is made by free radical solution polymerization in solution. Among such embodiments, at least one cationic polymer is made by free radical solution polymerization in an aqueous solvent.

The amount of cationic polymers in the personal care compositions of the invention may be 0.05 weight % or more, preferably 0.1 weight % or more, and more preferably 0.15 weight % or more, based on the total weight of the composition. By way of non-limiting example, the amount of cationic polymers in the personal care compositions of the invention may be 10 weight % or less, preferably 5 weight % or less, and more preferably 2.5 weight % or less, based on the total weight of the composition.

In certain embodiments, the inventive hair care compositions include a surfactant. Suitable surfactants include, for example, cationic, anionic, or amphoteric surfactants, and combinations thereof. In certain embodiments, the surfactant is a nonionic/emulsifier surfactant. In certain embodiments, the surfactant is a cationic surfactant, preferably behentrimonium chloride. In such embodiments, the surfactant may be present in an amount of from 0.1 to 10 weight %, preferably from 0.5 to 7 weight %, and more preferably from 1 to 4 weight %, by weight of the composition. In certain embodiments, the surfactant comprises a detergent surfactant. In such embodiments, the surfactant is present in an amount of from 1 to 25 weight %, preferably from 5 to 20 weight %, and more preferably from 7 to 18 weight %, by weight of the composition. Preferably, the detergent surfactant comprises an anionic surfactant in combination with an amphoteric surfactant. Suitable anionic surfactants include, for example, ammonium laureth sulfate, ammonium lauryl sulfate, sodium laureth sulfate, sodium lauryl sulfate, and combinations thereof. In certain embodiments, the anionic surfactant is present in an amount of from 1 to 25 weight %, preferably from 5 to 20 weight %, and more preferably from 7 to 15 weight %, by weight of the composition. In certain embodiments, the mixture is an anionic surfactant in combination with a second surfactant comprising at least one of disodium cocoamphodiacetate, decylglucoside, or cocamidopropyl betaine. In certain embodiments, the second surfactant is present in an amount of from 1 to 10 weight %, preferably from 1 to 8 weight %, and more preferably from 2 to 6 weigh %, by weight of the composition. In certain preferred embodiments, the surfactant is a mixture of sodium laureth sulfate (such as is commercially available from Cognis under the trade name STANDAPOL ES) and disodium cocoamphodiacetate (such as is commercially available from Henkel under the trade name VELVETEX CDC). In certain embodiments in which the surfactant is a mixture of sodium laureth sulfate and disodium cocoamphodiacetate, the ratio of sodium laureth sulfate to disodium cocoamphodiacetate is in a range from 9:1 to 2:1, preferably about 6:1.

In certain embodiments, the inventive hair care compositions include a rheology modifier. Suitable rheology modifiers include, for example, modified or unmodified carboxyvinyl polymers (e.g., the products sold under the names CARBOPOL and PEMULEN (INCI name: Acrylates/C10-30 alkyl acrylate crosspolymer; available from Noveon)), polyacrylates and polymethacrylates (e.g., the products sold under the names LUBRAJEL and NORGEL (commercially available from Guardian) or HISPAGEL (commercially available from Hispano Chimica)), polyacrylamides, 2-acrylamido-2-methylpropanesulfonic acid polymers and polymers (which are optionally crosslinked and/or neutralized (e.g., the poly(2-acrylamido-2-methylpropane-sulfonic acid) sold by Clariant (INCI name: ammonium polyacryldimethyltauramide)), emulsified crosslinked anionic polymers of acrylamide and AMPS (e.g., those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate polymer/Isohexadecane/Polysorbate 80; from Seppic)), polysaccharide biopolymers (e.g., xanthan gum, guar gum, carob gum, acacia gum, scleroglucans, chitin and chitosan derivatives, carrageenans, gellans, alginates, celluloses (e.g., microcrystalline cellulose), cellulose derivatives, associative polymers (e.g., associative polyurethanes), polymers comprising at least two hydrocarbon-based lipophilic chains comprising from 6 to 30 carbon atoms, separated with a hydrophilic sequence (e.g., the polyurethanes sold under the names SERAD FX1010, SERAD FX1100 and SERAD FX1035 (commercially available from Hüs America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (commercially available from The Dow Chemical Company)). In certain embodiments, the hair care compositions include a rheology modifier in an amount of from 0.05 to 5.0 weight %, preferably from 0.1 to 3.0 weight %, and more preferably 0.5 to 2.0 weight %, by weight of the composition.

In certain embodiments, the inventive hair care compositions include a cosmetic active. Suitable actives include, for example, anti-dandruff actives, sunscreen actives, moisturizing actives such as moisturizing oils, cleansing actives, detergent actives, vitamins, folic acid derivatives, exfoliating gents, deodorizing actives, bio-actives, fragrance actives, skin exfoliating actives, topical medicament actives, infrared (IR)-absorbing materials, acne medications, anti-frizz agents, hair waving/straightening agents, and combinations thereof. In certain embodiments, the hair care compositions include a cosmetic active in an amount of from 0.01 to 5 weight %, preferably from 0.1 to 3 weight %, and more preferably from 0.3 to 1 weight %.

The personal care compositions of the present invention may also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, acetone, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50% by weight of the dermatologically acceptable carrier, based on the total weight of the composition.

In certain embodiments, the personal care composition contains other optional ingredients, including, for example, emollients (e.g., hydrocarbon oils, esters, natural oils, silicones, or fatty acids), humectants, waxes, sensory modifiers, preservatives/antioxidants/chelating agents, reducing agents, pH adjusting agents/buffers/neutralizing agents, proteins/amino acids, plant extracts, natural ingredients, foaming agents, penetrants, volatiles/propellants/solvents/carriers, liquid vehicles/solvents/carriers, salts, anti-static agents, absorbents, colorants, and hard particles. The amount of optional ingredients effective for achieving the desired property provided by such ingredients can be readily determined by one skilled in the art.

As noted above, the hair care compositions of the present invention are highly effective as conditioning agents for providing smoothing of hair. They exhibit conditioning attributes on par with, if not better than, previously known additives for hair care applications, without the disadvantage of contributing to poor smoothness/sensory feel after deposition onto hair. Accordingly, the personal care compositions of the present invention are useful for the conditioning of hair. Thus, in one aspect the present invention provides that the hair care compositions may be used in a method for treating hair comprising applying to the hair a composition comprising the cationic polymers described herein and at least one cosmetically acceptable surfactant, rheology modifier, or cosmetic active.

In practicing the methods of the invention, the hair care compositions are generally administered topically by applying the compositions onto the hair in a conventional manner, such as by rubbing or massaging or combing into the hair with the composition. In the case of a leave-on (i.e., non-rinse-off) product, the composition is left in full concentration in contact with the hair. A person of ordinary skill in the art can readily determine the frequency with which the compositions should be applied. The frequency may depend, for example, on the extent of unmanageability of hair that an individual is encountering in a given day. By way of non-limiting example, administration on a frequency of at least once per day may be desirable.

Some embodiments of the invention will now be described in detail in the following Examples.

EXAMPLES

Example 1

Preparation of Exemplary Cationic Polymers

Exemplary cationic polymers in accordance with the present invention contain the components recited in Table 1.

TABLE 1

Exemplary Cationic Polymers

| Sample | Monomer (wt %) | | | |
|---|---|---|---|---|
|  | APTAC | AAm | DMAEMA | DMA |
| P1 (inventive) | 56.7 | 28.9 | 14.4 | — |
| P2 (inventive) | 50.0 | 16.7 | — | 33.3 |

APTAC = (3-acrylamidopropyl)trimethylammonium chloride
AAm = Acrylamide
DMAEMA = 2-(N,N-dimethylamino)ethyl methacrylate
DMA = N,N-dimethylacrylamide Inventive cationic polymers were prepared in a high-throughput mode using semi-continuous parallel pressure reactor (ScPPR) manufactured by Freeslate. In the synthesis of exemplary cationic polymer P1, aqueous solutions of APTAC (1.02 g), AAm (0.52 g), and DMAEMA (0.26 g) were used, with t-butyl hydroperoxide (t-BuOOH) and sodium formaldehyde sulfoxylate (SFS) used as an initiator in the amount of 0.15 weight % relative to the total amount of monomers. In the synthesis of exemplary cationic polymer P2, aqueous solutions of APTAC (0.90 g), AAm (0.30 g), and DMA (0.60 g) were used, with t-butyl hydroperoxide (t-BuOOH) and sodium formaldehyde sulfoxylate (SFS) used as an initiator in the amount of 0.15 weight % relative to the total amount of monomers. The total amount of the reaction mixture (including water) was 6.0 mL, and therefore the mixture contained 30% (wt/v) solids. The amount of residual monomers in polymers P1 and P2 was determined by HPLC. The column Luna C18 4.6×150 mm, 3 µm, and the guard column Luna C18 3×4 mm were used. Water and acetonitrile containing 0.08% trifluoroacetic acid (TFA) were used as a mobile phase, with the following gradient: (a) Time: 0-15 min; Acetonitrile: 025%; (b) Time: 15-21 min; Acetonitrile: 25%; (c) Time: 21-25 min; Acetonitrile: 25-0%. A constant flow rate of 1.0 mL/min was used during the whole run. A UV detector set at 195 nm, 205 nm, or 215 nm was used. This method showed that the conversion of all monomers was quantitative. Molecular weights of polymers were determined using gel permeation chromatography (GPC). The following parameters were used: Column: TSK-gel AlphaM (7.8 mm×30 cm, 13µ); Mobile phase: 0.5M $CH_3COOH$+0.1M $NaNO_3$ in water; Flow Rate: 0.55 mL/min; Temperature: 25° C.; Detector: RI; Sample concentration: 1 mg/mL in mobile phase; Calibration: Poly (ethylene oxide) (PEO) standards. The $M_w$ of polymer P1 was determined to be 735,527 with a viscosity of 519 cps (2.0 wt % polymer solution in water). The $M_w$ of polymer P2 was determined to be 669,173 with a viscosity of 7,552 cps (2.0 wt % polymer solution in water).

Example 2

Preparation of Exemplary and Comparative Hair Care Compositions

Exemplary (inventive samples E1 and E2) and comparative (comparative sample C1) hair care compositions contain the components recited in Table 2.

TABLE 2

Exemplary Hair Care Compositions

| Component | INCI Name | E1 (wt %) | E2 (wt %) | C1 (wt %) |
|---|---|---|---|---|
| DI Water | DI Water | 14.70 | 14.70 | 14.70 |
| P1 (2%) | — | 15.00 | — | — |
| P2 (2%) | — | — | 15.00 | — |
| SoftCAT SL 5[1] (2%) | Polyquaternium-67 | — | — | 15.00 |
| Standapol ES-2 (25.5%)[1] | Sodium laureth sulfate | 60.78 | 60.78 | 60.78 |
| Velvetex CDC (38.5%)[3] | Disodium cocoamphodiacetate | 6.92 | 6.92 | 6.92 |
| Citric acid (10%) | — | 2.20 | 2.20 | 2.20 |
| Gyldant[4] | DMDM hydantoin | 0.40 | 0.40 | 0.40 |
| Total | | 100 | 100 | 100 |

[1]Available from The Dow Chemical Company
2 Available from BASF
[3]Available from Henkel
[4]Available from Lonza An aqueous solution of each polymer (i.e., inventive P1, inventive P2, and SoftCat SL 5) was prepared by adding water to the dried polymer to give a 2.0 wt % polymer dispersion that was magnetically stirred, first at ambient temperature for 30 minutes, and then at 65° C. for 30 minutes. A master batch of surfactants was prepared from Standapol ES-2 (73.7 wt %) and Velvetex CDC (8.4 wt %) in water (17.9 wt %). This mixture was stirred at ambient temperature for 30 minutes to give a clear surfactant solution. Aliquots (4.3 g each) of this surfactant were placed into separate ScPPR glass insets, and each 2% polymer solution (0.75 g) was added into a separate inset. The insets with mixtures were capped, heated to 65° C., and stirred at 1,400 rpm for 20 minutes. The stirring was then stopped, and citric acid was added into each inset, and the resulting mixtures were stirred at ambient temperature at 1,400 rpm for 10 minutes. The temperature set point was then reduced to 14° C. and the mixtures were stirred at 1,400 rpm for 15 minutes. The stirring was then stopped, and Glydant preservative was added into each inset, and the mixtures were stirred at 1,400 rpm for 2 minutes. The insets with the resulting formulations were then removed from the ScPPR and sealed.

Example 3

Evaluation of Shampoo Formulations

The formulations as prepared in Examples 1-2 above were evaluated for appearance and wet combing force reduction using miniature tensile testers. Hair tresses (about 5 g) were washed with either a surfactant solution alone (0.5 g), or with a shampoo formulation that contained surfactants and a cationic polymer. The treated hair tresses were rinsed at constant temperature and attached to the tensile tester. The comb was pulled through each tress at a pulling speed of 40 mm/min and the pulling path length of 160 mm. The force required to comb the hair tress was measured as the area below the curve. The efficiency of a conditioning polymer in shampoo formulation was determined as a reduction of combing friction when hair is treated with such formulations, relative to the combing friction of wet hair washed with in shampoo without polymer. The result is reported as a wet combing work done (WCWD; wet-comb area below the tensile curve). The results are shown in Table 3.

TABLE 3

Evaluation of Shampoo Formulations with Cationic Polymers

| Sample | Shampoo Appearance | WCWD |
|---|---|---|
| E1 | Slightly Hazy | 3,089 |
| E2 | Milky | 1,823 |
| C1 | Clear | 5,740 |

As shown in Table 3 above, hair tresses treated with inventive shampoo formulations E1 and E2 containing the inventive cationic polymers demonstrated lower wet combing work done than the comparative formulation containing benchmark SoftCAT SL-5. These results demonstrate that the inventive hair care compositions containing the inventive polymers provide superior wet combing performance when applied to hair.

Example 4

Preparation of Exemplary and Comparative Hair Care Compositions

Exemplary (inventive sample E3) and comparative (comparative sample C2) hair care compositions contain the components recited in Table 4.

TABLE 4

Exemplary Hair Care Compositions

| Component | INCI Name | E3 (wt %) | C2 (wt %) |
|---|---|---|---|
| DI Water | DI Water | 10.50 | 14.70 |
| P2 (1.5 %) | — | 20.00 | — |
| SoftCAT SL 5[1] (2.0%) | Polyquaternium-67 | — | 15.00 |
| Standapol ES-2 (25.5%)[1] | Sodium laureth sulfate | 60.78 | 60.78 |
| Velvetex CDC (38.5%)[3] | Disodium cocoamphodiacetate | 6.92 | 6.92 |
| Citric acid (10%) | — | 2.20 | 2.20 |
| Gyldant[4] | DMDM hydantoin | 0.40 | 0.40 |
| Total | | 100 | 100 |

[1]Available from The Dow Chemical Company
2 Available from BASF
[3]Available from Henkel
[4]Available from Lonza An aqueous solution of inventive polymer P2 was prepared by adding water to the dried polymer to give a 1.5 wt % polymer dispersion. The polymers were hydrated for about 30 minutes at room temperature, followed by about 30 minutes at 65° C. Sodium laureth sulfate and disodium cocoamphodiacetate were added into a glass jar with a stir rod. The mixture was slowly heated to 60° C. while mixing with an overhead stirrer at approximately 500 rpm until a surfactant solution was formed. After 15 minutes, the mixture was slowly cooled to 35° C. via a cool water bath. Either polymer P2 or SoftCAT SL 5 was then added to the polymer solution to 0.30 weight % and stirred for an additional 30 minutes. Citric acid (10 wt %) was then added to the mixture and stirred for an additional 10 minutes. Glydant and water were then added and the mixture was stirred for about 15 minutes at 500 rpm.

Example 5

Objective Wet Comb Evaluation

The formulations as prepared in Examples 1 and 4 above were evaluated for wet combing force reduction using miniature tensile testers. Hair tresses (about 5 g) were washed with either a surfactant solution alone (0.5 g), or with a shampoo formulation that contained surfactants and a cationic polymer. The treated hair tresses were rinsed at constant temperature and attached to the tensile tester. The comb was pulled through each tress at a pulling speed of 40 mm/min and the pulling path length of 160 mm. The force required to comb the hair tress was measured as the area below the curve. The efficiency of a conditioning polymer in shampoo formulation was determined as a reduction of combing friction when hair is treated with such formulations, relative to the combing friction of wet untreated hair. The result is reported as a wet combing work done (WCWD; wet-comb area below the tensile curve) or as percentage of work reduction in wet combing (RWC) relative to the wet combing work for untreated wet hair tress as a control:

% work reduction=[area(no polymer)−area(shampoo)]/area(no polymer)

As shown in FIG. 1, hair tresses treated with inventive shampoo formulation E3 demonstrated lower wet combing work done than the comparative formulation C2. These results demonstrate that the inventive hair care compositions containing the inventive polymers provide superior wet combing performance when applied to hair.

What is claimed is:

1. A hair care composition comprising:
   (a) a cationic polymer consisting of polymerized units derived from
      (i) 45 to 65 weight % of (3-acrylamidopropyl)trimethylammonium chloride (APTAC),
      (ii) 10 to 65 weight % of (meth)acrylamide monomers, and
      (iii) 2 to 30 weight % of polar non-ionic derivatives of acrylic monomers; and
   (b) at least one cosmetically acceptable surfactant, rheology modifier, or cosmetic active.

2. The hair care composition of claim 1, wherein the personal care composition is a leave-on conditioner, a hair treatment formulation, or a combing cream.

3. The hair care composition of claim 1, wherein the polar non-ionic derivatives of acrylic monomers comprise at least one of alkyl (meth)acrylate or acrylamide comprises at least one of 2-(dimethylamino)ethyl acrylate, 2-(dimethylamino) ethyl methacrylate, and 3-(dimethylamino)propyl acrylate.

4. The hair care composition of claim 1, wherein the cationic polymer is present in a range of from 0.05 to 10 weight %, by weight of the composition.

5. A method for treating hair comprising contacting hair with a personal care composition according to claim 1.

6. The method of claim 5, wherein the personal care composition is a leave-on conditioner, a hair treatment formulation, or a combing cream.

* * * * *